(12) United States Patent
Goodall et al.

(10) Patent No.: US 7,831,448 B1
(45) Date of Patent: *Nov. 9, 2010

(54) METHOD AND APPARATUS FOR INTER-PHARMACY WORKLOAD BALANCING USING RESOURCE FUNCTION ASSIGNMENTS

(75) Inventors: Charles Goodall, Hawthorn Woods, IL (US); Nimesh Jhaveri, Grayslake, IL (US); Russell Alan Wielgos, Wauconda, IL (US)

(73) Assignee: Walgreen Co., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/766,671

(22) Filed: Apr. 23, 2010

Related U.S. Application Data

(63) Continuation of application No. 11/253,096, filed on Oct. 18, 2005, now Pat. No. 7,734,478.

(51) Int. Cl.
*G06Q 10/00* (2006.01)
*G06Q 50/00* (2006.01)

(52) U.S. Cl. ......................................................... 705/2
(58) Field of Classification Search ..................... 705/2, 705/4, 7, 9; 710/6; 718/105
See application file for complete search history.

(56) References Cited

U.S. PATENT DOCUMENTS

| | | | |
|---|---|---|---|
| 4,457,772 A | 7/1984 | Haynes et al. | |
| 4,852,001 A | 7/1989 | Tsushima et al. | |
| 5,053,970 A | 10/1991 | Kurihara et al. | |
| 5,072,383 A | 12/1991 | Brimm et al. | |
| 5,260,868 A | 11/1993 | Gupta et al. | |
| 5,289,370 A | 2/1994 | Lirov | |
| 5,337,919 A | 8/1994 | Spaulding et al. | |
| 5,548,518 A | 8/1996 | Dietrich et al. | |
| 5,559,710 A | 9/1996 | Shahraray et al. | |
| 5,597,995 A | 1/1997 | Williams et al. | |
| 5,615,121 A | 3/1997 | Babayev et al. | |
| 5,619,991 A | 4/1997 | Sloane | |
| 5,630,070 A | 5/1997 | Dietrich et al. | |
| 5,737,539 A | 4/1998 | Edelson et al. | |
| 5,737,728 A | 4/1998 | Sisley et al. | |
| 5,748,907 A | 5/1998 | Crane | |
| 5,758,095 A | 5/1998 | Albaum et al. | |

(Continued)

FOREIGN PATENT DOCUMENTS

EP    0 921 488 A1    6/1999

(Continued)

OTHER PUBLICATIONS

Colchamiro, "Independents Look To Go Online," American Druggist, Sep. 1999, pp. 1-3.

(Continued)

*Primary Examiner*—Gerald J. O'Connor
*Assistant Examiner*—John A Pauls
(74) *Attorney, Agent, or Firm*—Francis C. Kowalik, Walgreen Co.; Marshall, Gerstein & Borun LLP; Randall G. Rueth

(57) ABSTRACT

The system distributes workload amongst a plurality of pharmacy resources that are connected by a computer network. Work orders are queued at each pharmacy resource and redistributed based on existing workload distribution, capacity of pharmacy resources, and/or product demand.

19 Claims, 13 Drawing Sheets

U.S. PATENT DOCUMENTS

| | | | |
|---|---|---|---|
| 5,765,139 | A | 6/1998 | Bondy |
| 5,790,785 | A | 8/1998 | Klug et al. |
| 5,797,515 | A | 8/1998 | Liff et al. |
| 5,801,755 | A | 9/1998 | Echerer |
| 5,826,236 | A | 10/1998 | Narimatsu et al. |
| 5,826,252 | A | 10/1998 | Wolters, Jr. et al. |
| 5,845,255 | A | 12/1998 | Mayaud |
| 5,852,259 | A | 12/1998 | Yanase et al. |
| 5,907,493 | A | 5/1999 | Boyer et al. |
| 5,911,687 | A | 6/1999 | Sato et al. |
| 5,915,240 | A | 6/1999 | Karpf |
| 5,924,074 | A | 7/1999 | Evans |
| 5,946,883 | A | 9/1999 | Yuyama et al. |
| 5,954,640 | A | 9/1999 | Szabo |
| 5,963,911 | A | 10/1999 | Walker et al. |
| 5,970,462 | A | 10/1999 | Reichert |
| 5,987,519 | A | 11/1999 | Peifer et al. |
| 6,067,524 | A | 5/2000 | Byerly et al. |
| 6,078,912 | A | 6/2000 | Buerger et al. |
| 6,112,182 | A | 8/2000 | Akers et al. |
| 6,202,080 | B1 | 3/2001 | Lu et al. |
| 6,202,923 | B1 | 3/2001 | Boyer et al. |
| 6,208,973 | B1 | 3/2001 | Boyer et al. |
| 6,256,550 | B1 | 7/2001 | Wu et al. |
| 6,266,655 | B1 | 7/2001 | Kalyan |
| 6,294,999 | B1 | 9/2001 | Yarin et al. |
| 6,311,163 | B1 | 10/2001 | Sheehan et al. |
| 6,330,491 | B1 | 12/2001 | Lion |
| 6,347,329 | B1 | 2/2002 | Evans |
| 6,364,517 | B1 | 4/2002 | Yuyama et al. |
| 6,370,841 | B1 | 4/2002 | Chudy et al. |
| 6,381,577 | B1 | 4/2002 | Brown |
| 6,397,190 | B1 | 5/2002 | Goetz |
| 6,421,650 | B1 | 7/2002 | Goetz et al. |
| 6,438,451 | B1 | 8/2002 | Lion |
| 6,463,417 | B1 | 10/2002 | Schoenberg |
| 6,464,142 | B1 | 10/2002 | Denenberg et al. |
| 6,477,442 | B1 | 11/2002 | Valerino, Sr. |
| 6,493,427 | B1 | 12/2002 | Kobylevsky et al. |
| 6,496,427 | B2 | 12/2002 | Kojima et al. |
| 6,523,009 | B1 | 2/2003 | Wilkins |
| 6,539,281 | B2 | 3/2003 | Wan et al. |
| 6,564,121 | B1 | 5/2003 | Wallace et al. |
| 6,625,952 | B1 | 9/2003 | Chudy et al. |
| 6,665,740 | B1 | 12/2003 | Mason, Jr. et al. |
| 6,711,460 | B1 | 3/2004 | Reese |
| 6,735,497 | B2 | 5/2004 | Wallace et al. |
| 6,741,724 | B1 | 5/2004 | Bruce et al. |
| 6,874,684 | B1 | 4/2005 | Denenberg et al. |
| 6,947,900 | B2 | 9/2005 | Giordano, III et al. |
| 7,058,584 | B2 | 6/2006 | Kosinski et al. |
| 7,111,780 | B2 | 9/2006 | Broussard et al. |
| 7,139,639 | B2 | 11/2006 | Broussard et al. |
| 2001/0009005 | A1 | 7/2001 | Godin et al. |
| 2002/0019786 | A1 | 2/2002 | Gonzalez et al. |
| 2002/0052770 | A1 | 5/2002 | Podrazhansky |
| 2002/0062175 | A1 | 5/2002 | Lion |
| 2002/0062230 | A1 | 5/2002 | Morag et al. |
| 2002/0120573 | A1 | 8/2002 | McCormick |
| 2002/0153411 | A1 | 10/2002 | Wan et al. |
| 2002/0188467 | A1 | 12/2002 | Eke |
| 2002/0198454 | A1 | 12/2002 | Seward et al. |
| 2003/0074234 | A1 | 4/2003 | Stasny |
| 2003/0109950 | A1 | 6/2003 | Andrade et al. |
| 2003/0149599 | A1 | 8/2003 | Goodall et al. |
| 2003/0179287 | A1 | 9/2003 | Kozic et al. |
| 2003/0225595 | A1 | 12/2003 | Helmus et al. |
| 2004/0019794 | A1 | 1/2004 | Moradi et al. |
| 2004/0117046 | A1 | 6/2004 | Colle et al. |
| 2004/0133705 | A1 | 7/2004 | Broussard et al. |
| 2004/0172289 | A1 | 9/2004 | Kozic et al. |
| 2004/0220829 | A1 | 11/2004 | Baharav et al. |
| 2004/0221034 | A1 | 11/2004 | Kausik et al. |
| 2004/0260577 | A1 | 12/2004 | Dahlin et al. |
| 2005/0075902 | A1 | 4/2005 | Wager et al. |
| 2005/0125798 | A1 | 6/2005 | Peterson |
| 2006/0041330 | A1 | 2/2006 | Ansari et al. |
| 2006/0276933 | A1 | 12/2006 | Chavez et al. |
| 2006/0287906 | A1 | 12/2006 | McGillin |

FOREIGN PATENT DOCUMENTS

| | | |
|---|---|---|
| JP | 361217880 A | 9/1986 |
| WO | WO-96/13790 A1 | 5/1996 |
| WO | WO-01/08393 A1 | 2/2001 |

OTHER PUBLICATIONS

McNaughton, "Can Net Drugstores Outpace The Chains?" CNET News.com, Feb. 24, 1999, 1 page.

Wolverton, "Online Pharmacies Partner For Power," CNET News.com, Oct. 8, 1999, pp. 1-2.

U.S. Appl. No. 09/715,872, filed Nov. 15, 2000, entitled "Apparatus And Method For Accessing Pharmacy Information And Ordering Prescriptions."

U.S. Appl. No. 11/252,775, filed Oct. 18, 2005, entitled "Method And Apparatus For Inter-Pharmacy Workload Balancing."

U.S. Appl. No. 11/253,252, filed Oct. 18, 2005, entitled "System For Separating And Distributing Pharmacy Order Processing."

U.S. Appl. No. 11/252,947, filed Oct. 18, 2005, entitled "System For Separating And Distributing Pharmacy Order Processing For Compound Medication."

U.S. Appl. No. 11/252,776, filed Oct. 18, 2005, entitled "System For Separating And Distributing Pharmacy Order Processing For Specialty Medication."

U.S. Appl. No. 11/253,253, filed Oct. 18, 2005, entitled "System For Separating And Distributing Pharmacy Order Processing For Out Of Stock Medication."

U.S. Appl. No. 11/252,759, filed Oct. 18, 2005, entitled "System For Separating And Distributing Pharmacy Order Processing For Medication Payments."

U.S. Appl. No. 11/253,185, filed Oct. 18, 2005, entitled "System For Separating And Distributing Pharmacy Order Processing For Prescription Verification."

"The Virtual Pharmacist," *Rural Electric*, vol. 60, No. 6, Mar. 2002, p. 20.

"Optimize your Enterprise for Maximum Profitability," NDCHEALTH, May 5, 2005, 4 pages.

"File Locking," www.wikipedia.org/wili/file_locking obtained via web.archive.com.

Anonymous, "CVS, Merck-Medco in E-commerce Alliance," Chain Drug Review, 21(18):2 (1999).

Anonymous, "Name Change Reflects CVS' Commitment to E-commerce," Chain Drug Review, 21(15):2 (1999).

Walgreens On-line Prefills (Website Printout Packet-printed Jul. 5, 2006) archived as Jun. 17, 1998, p. 1-13.

Office Action issued in U.S. Appl. No. 11/253,185 dated Aug. 4, 2009.

Final Office Action issued in U.S. Appl. No. 11/253,185 dated Jan. 8, 2010.

Office Action issued in U.S. Appl. No. 11/252,776 dated Sep. 28, 2009.

Final Office Action issued in U.S. Appl. No. 11/252,776 dated Apr. 22, 2010.

Office Action issued in U.S. Appl. No. 11/252,947 dated Sep. 2, 2009.

Office Action issued in U.S. Appl. No. 11/252,947 dated Mar. 17, 2010.

Office Action issued in U.S. Appl. No. 11/253,252 dated Sep. 3, 2009.

Final Office Action issued in U.S. Appl. No. 11/253,252 dated Mar. 5, 2010.

Office Action issued in U.S. Appl. No. 11/253,253 dated May 13, 2008.

Final Office Action issued in U.S. Appl. No. 11/253,253 dated Jan. 6, 2009.

Office Action issued in U.S. Appl. No. 11/253,253 dated Jul. 20, 2009.
Final Office Action issued in U.S. Appl. No. 11/253,253 dated Mar. 9, 2010.
Office Action issued in U.S. Appl. No. 11/252,775 dated Apr. 30, 2009.
Final Office Action issued in U.S. Appl. No. 11/252,775 dated Sep. 29, 2009.
Office Action issued in U.S. Appl. No. 11/252,759 dated Jul. 9, 2009.
Final Office Action issued in U.S. Appl. No. 11/252,759 dated Jan. 15, 2010.

| Pharmacist Resource | Location | Schedule | Expertise Level | Assignment |
|---|---|---|---|---|
| 1 | Retail 1 | Available | Retail | General Retail |
| 2 | Facility 4 | Unavailable | Retail/Compound | Not Assigned |
| 3 | Home | Available | Specialty Drug | Specialty Drug |
| 4 | Home | Unavailable | Retail | Unavailable |

METHOD AND APPARATUS FOR INTER-PHARMACY WORKLOAD BALANCING USING RESOURCE FUNCTION ASSIGNMENTS

This is a continuation of U.S. application Ser. No. 11/253,096, filed Oct. 18, 2005, the entire disclosure of which is incorporated herein by reference.

TECHNICAL FIELD

The present disclosure generally relates to workload balancing for pharmacy resources connected by a computer network.

BACKGROUND

Existing pharmacy networks performing order processing may suffer from inefficient distribution of workload. Many factors may contribute to this inefficient distribution. For example, a first location may receive a greater amount of order volume than a second location, equipment at a first facility may be more efficient than in a second facility, or employees at a first location may be more efficient (e.g., better skilled) than in a second retail location. While these pharmacy networks may benefit from redistributing workload, existing pharmacy information systems do not provide this functionality.

Certain retail industries, such as pharmacies, process discrete product orders on the premises of a retail store. Processing of the order may be separated into information processing of the order and physical processing of the order. Because information processing of the order may not need to be performed completely by a single resource and/or at a particular location, the information processing portion of the order fulfillment process may be sent to another resource for execution, e.g., another retail store. This redistribution of work may be especially useful in a franchise retail store network where a corporate entity may have the power to manage distribution and completion of work within the network. However, a distribution system and method may be required to obtain such a workload distribution objective.

SUMMARY

The method and system claimed in the present application provide a process for distributing workload amongst a plurality of pharmacy resources that are connected by a computer network. While the specific method and system will be described to apply to a pharmacy retail network embodiment, it is emphasized that this process may be applied to other retail industries as well.

One embodiment involves queuing pharmacy prescription orders at each pharmacy resource. Metrics may be taken by a client or a server computer, or may even be taken manually, to determine the workload for each pharmacy resource in the network. A distribution of the current workload may be generated to assist in determining which resources may be overworked and which resources may be under worked. This distribution information may be used to determine a more efficient target workload distribution. The target workload distribution may be implemented by rerouting workload between pharmacy resources in the network. In one embodiment, this may be performed by designating pharmacies as senders or receivers and routing work orders from sender queues to receiver queues.

In another embodiment, workload may be redistributed based on a demand for a drug type and/or a capacity of a pharmacy resource to process orders for that drug type. In this embodiment a pharmacy resource may be assigned or designated a specific order process function to perform and work orders may be routed to the pharmacy resource for processing a portion of work related to the function. For example, a pharmacy resource may be designated a receiver for prescription orders having a certain drug type. Consequently, work orders for the drug type may be rerouted to the pharmacy resource for at least a portion of the order processing.

BRIEF DESCRIPTION OF THE DRAWINGS

FIG. 12 illustrates a resource assignment table; and

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
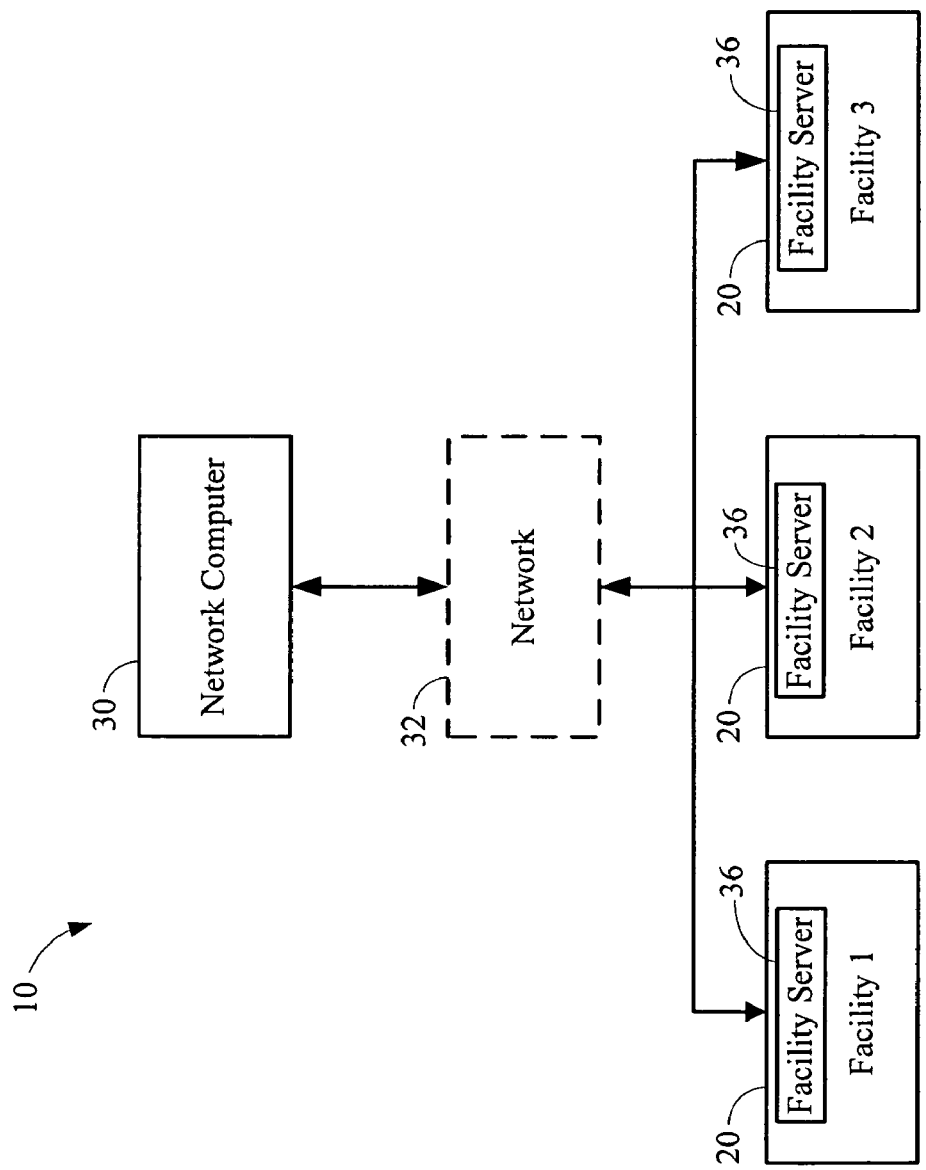
FIG. 1 illustrates a diagram of a data network that may operate in accordance with a described embodiment.

FIG. 1 illustrates an embodiment of a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
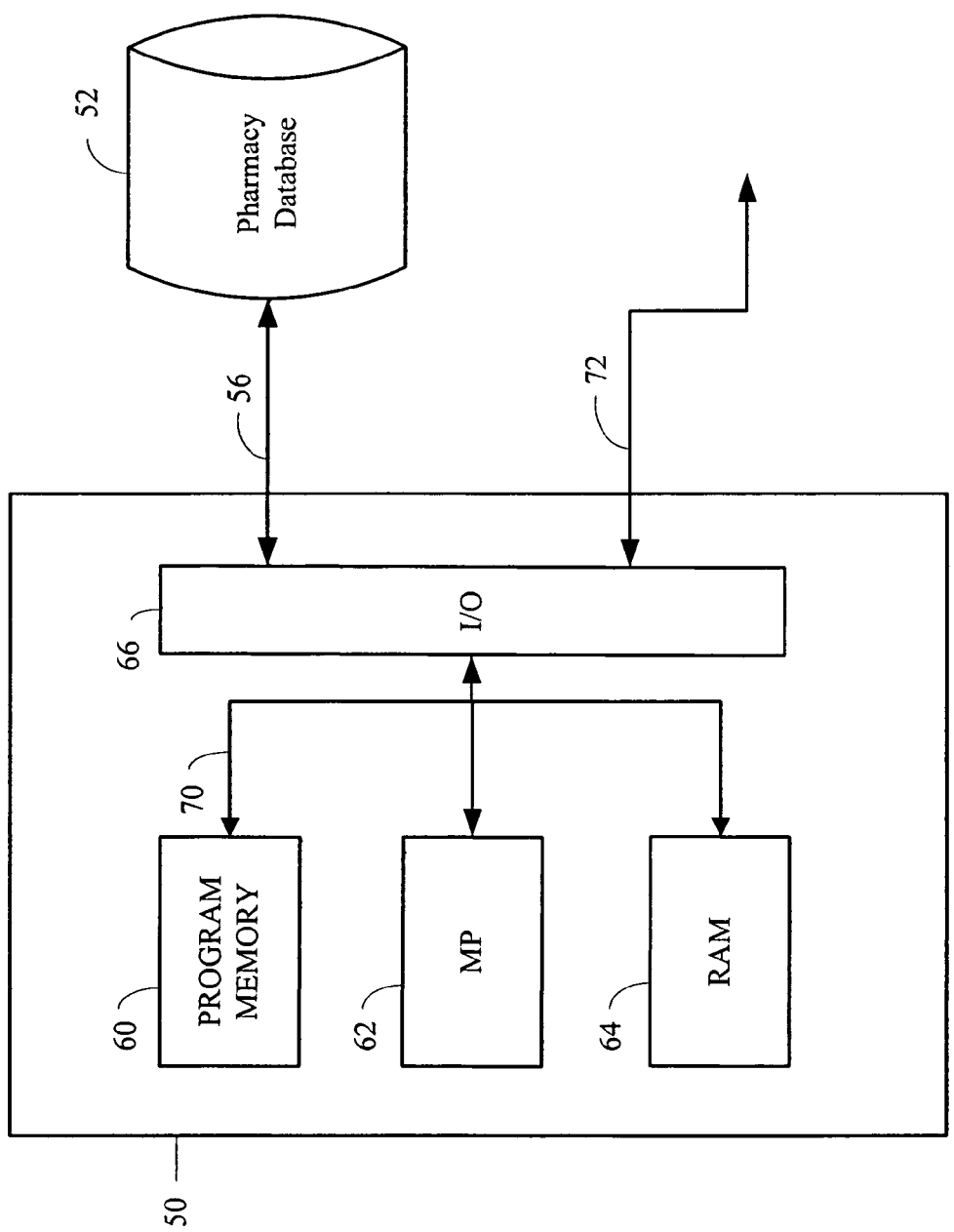
FIG. 2 illustrates an embodiment of the network computer of FIG. 1.

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAIVIs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
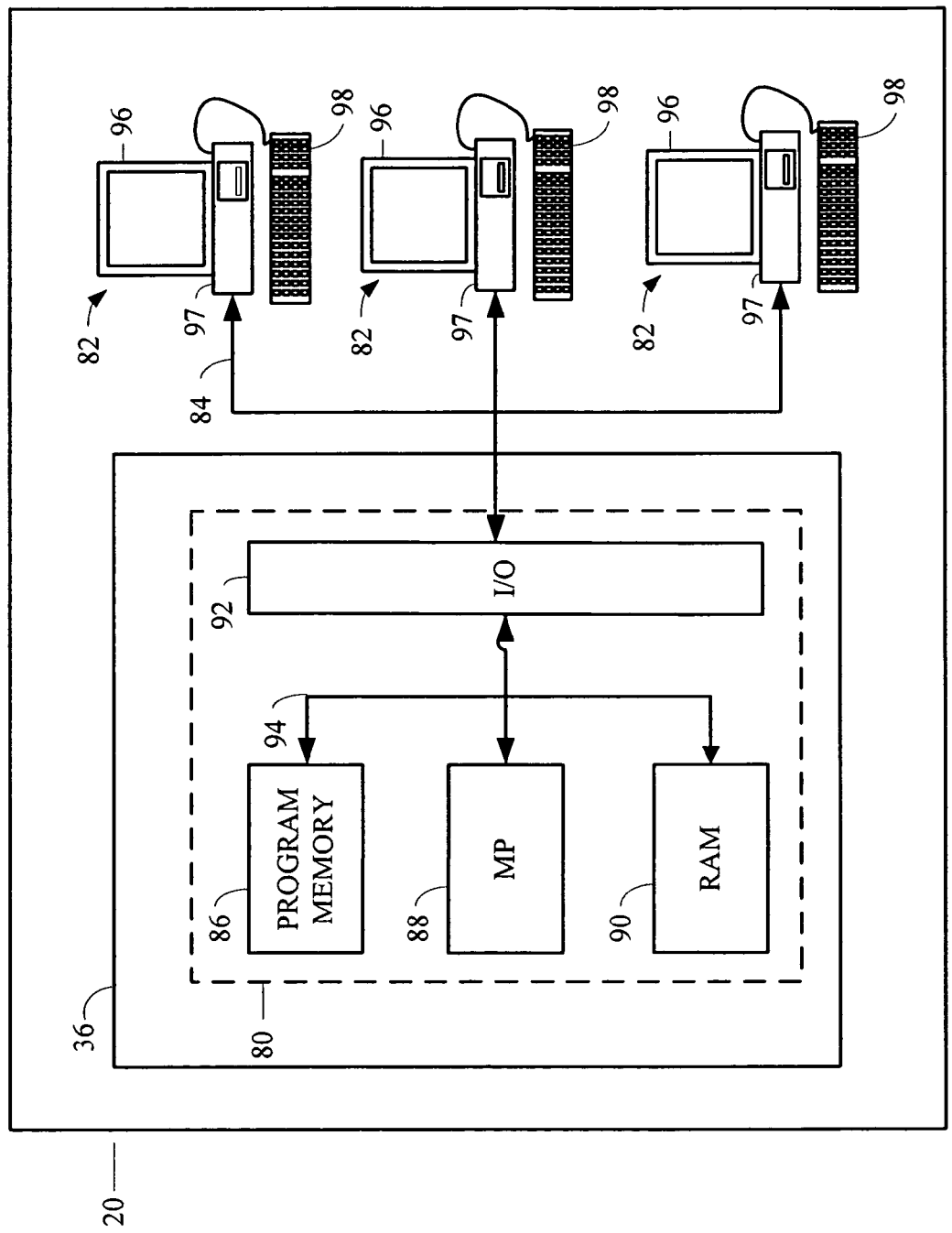
FIG. 3 illustrates an embodiment of a pharmacy computer system.

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAIVIs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Figure 4:
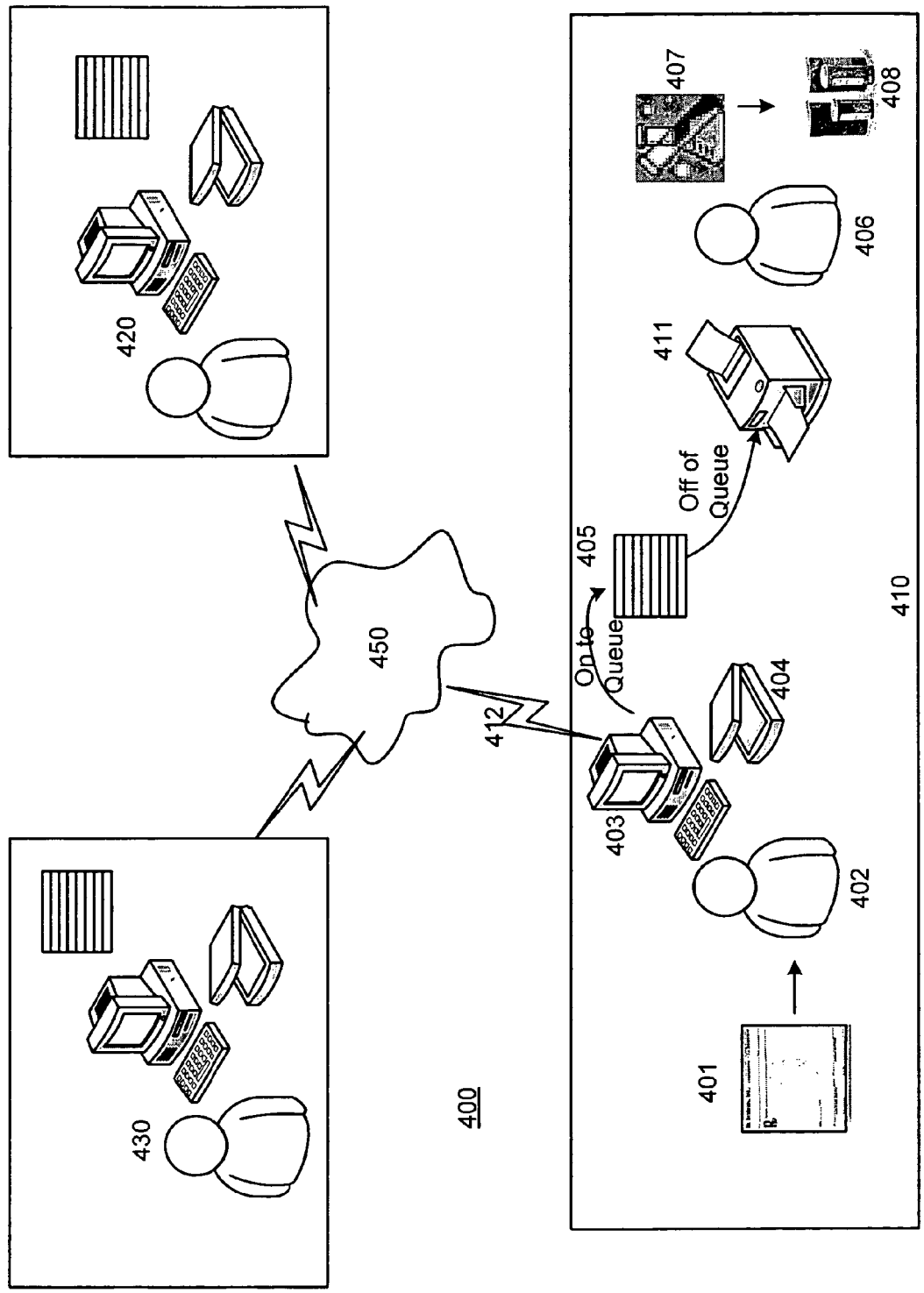
FIG. 4 illustrates a pharmacy network embodiment.

FIG. 4 illustrates a pharmacy network 400 comprising a network computer 403, or network node, at each pharmacy location 410, 420, 430. This network computer may be connected to a scanner 404 and may have a connection link 412 to other pharmacy computers via a network 450. An employee 402 may receive a physical prescription order 401 from a customer at a particular pharmacy location 410 and input the prescription order 401 into the network computer 403 for that location. The employee 402 may scan the prescription as well as associated documents into the computer in addition to manually entering prescription information. The network computer 403 may have a set of processed prescriptions stored in a queue 405. The employee 402 may continue entering prescriptions into the queue 405 as they are received.

The prescriptions that have finished information processing are ready for physical processing to fill the prescription. The physical process of filing the prescription at the retail location may begin with the printing of a prescription label 411 from the queue 405. The scheduling and printing may be automated, and may be in accordance with the process described in U.S. application Ser. No. 11/253,252 entitled, "System For Separating And Distributing Pharmacy Order Processing," taking into account desired delivery times, customer waiting requirements, etc. Based on the label 411, and/or instruction set, a pharmacist 406 may physically prepare the drug by mixing compounds 407 to produce a final prescription drug, receive pre-processed compounds and formulations, or otherwise obtain the materials necessary to fill the prescription 408 based on the label. The queue 405 may be operated as a first in, first out (FIFO) stack process, where newly entered orders are placed on top of the queue while orders are pulled from the bottom of the queue for filling.

Figures 5A, 5B:
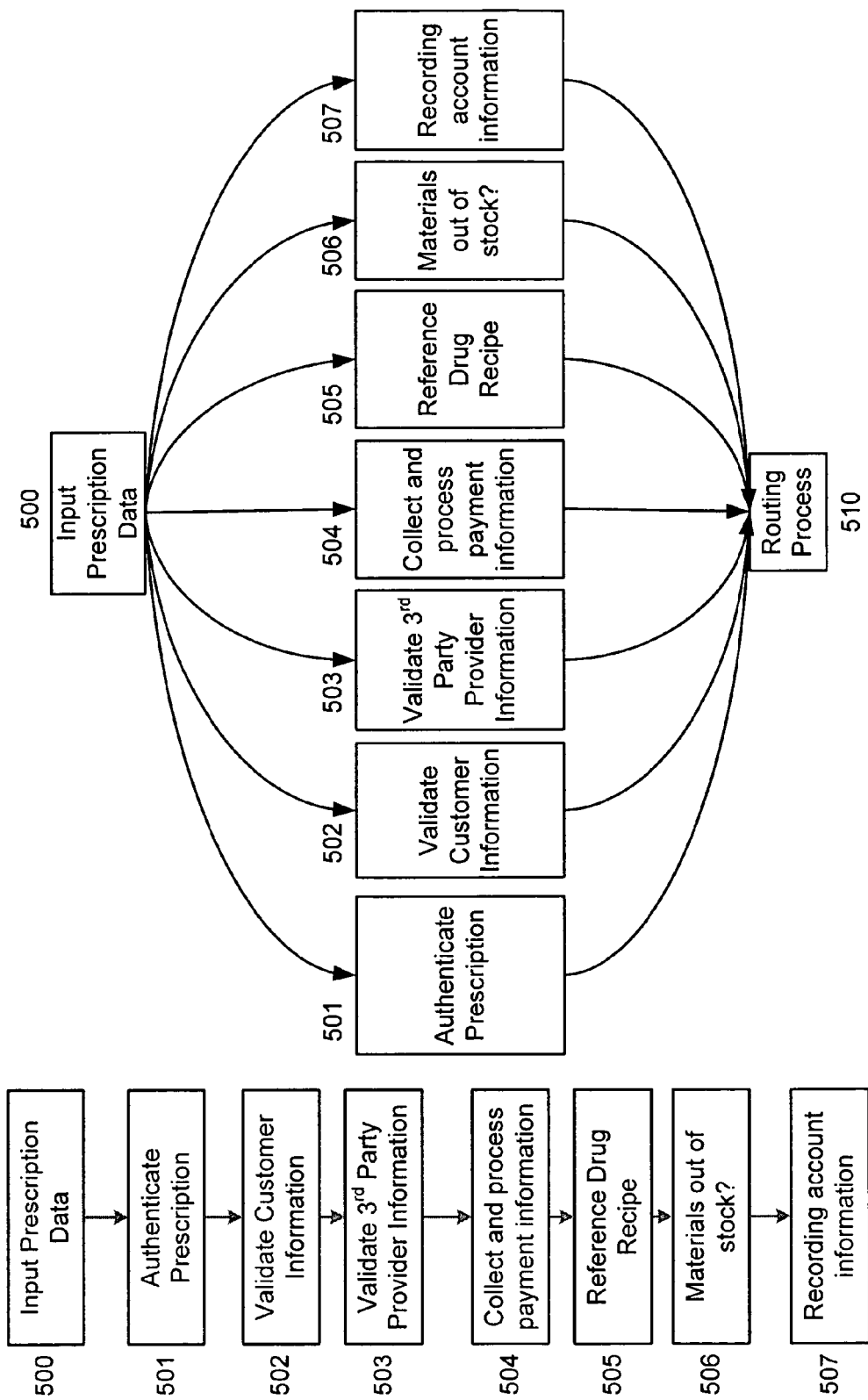
FIGS. 5a and 5b illustrate possible pharmacy information processing flows.

In a pharmacy embodiment, work for each prescription order may be divided between physical preparation of a prescribed drug and the processing of prescription information required to prepare the drug. For example, referring to FIG. 4, physical preparation involves performing various tasks generally illustrated by 406, 407, and 408. Information processing is captured by 401-405. The information processing may be further divided as illustrated in FIG. 5a. FIG. 5a illustrates a possible segmentation and processing of information. The information processing of a prescription may include, but is not limited to, inputting prescription data 500, authenticating a prescription 501, validating customer information 502, validating third-party provider information 503, collecting payment information 504, referencing drug information 505, determining out-of-stock status of materials 506, and entering accounting information into an accounting database 507.

The information processing portion of work may be performed by multiple pharmacy resources, e.g., pharmacy employees, at different locations. Therefore, an embodiment may distribute this work portion amongst a number of pharmacy resources to improve overall network processing efficiency. While FIG. 5a illustrates that these processing blocks may be performed serially, these steps may be performed in parallel as illustrated in FIG. 5b. FIG. 5b illustrates that after any one of the work portions are performed, the work for that order may be routed 510 to another resource or location for further processing, e.g., for finishing another portion of the work.

Referring again to FIG. 4, a portion or all of the information processing associated with a prescription may be routed to a different pharmacy resource, such as store locations 420 or 430, than the location 410 in which the prescription is first entered. Once the information processing is completed, the instructions may be sent to another resource or location for label printing and physical preparation, including the originating store. Alternatively, the information processing resource may complete the prescription by physically preparing and delivering the drug at that location. Alternatively, delivery may occur, for example, from a mail service facility or home delivery facility of the pharmacy network. Delivery may be completed at a different store, when the customer chooses to pick up the order from another store.

The process of distributing information processing for a network of pharmacies will now be described. The workload for each pharmacy may be determined in a number of ways. Generally, workload may be determined by determining the amount of work performed in a given amount of time. Because one of the described embodiments is concerned with pharmacy related work and pharmacy efficiency, a workload calculation that uses a pharmacy related work factor and pharmacy efficiency factor is useful. Pharmacy workload may be determined as the ratio of the number of prescriptions filled to the total number of man hours for a given store:

$$\text{Pharmacy\_Workload} = \frac{\text{Number\_of\_prescriptions}}{\text{Total\_man\_hours}}$$

Man hours may be calculated as a unit of one hour's work performed by an average pharmacy employee, which may be adjusted or weighted based on the type of employee, e.g., a pharmacist, a pharmacy technician, clerks, etc.

The prescription volume may be manually tabulated, or determined by a computer. For example, the network computer may simply sum the number of prescriptions filled for each day and use this number. The computer may calculate the average number of prescriptions being fulfilled over a shorter or longer time period as desired. If a manual collection system is implemented, a reasonable amount of time for collecting workload data may be a 1-2 week period. For automated systems, the collection time may be made arbitrarily small, e.g., on the order of hours, minutes, seconds, etc.

Figure 6:
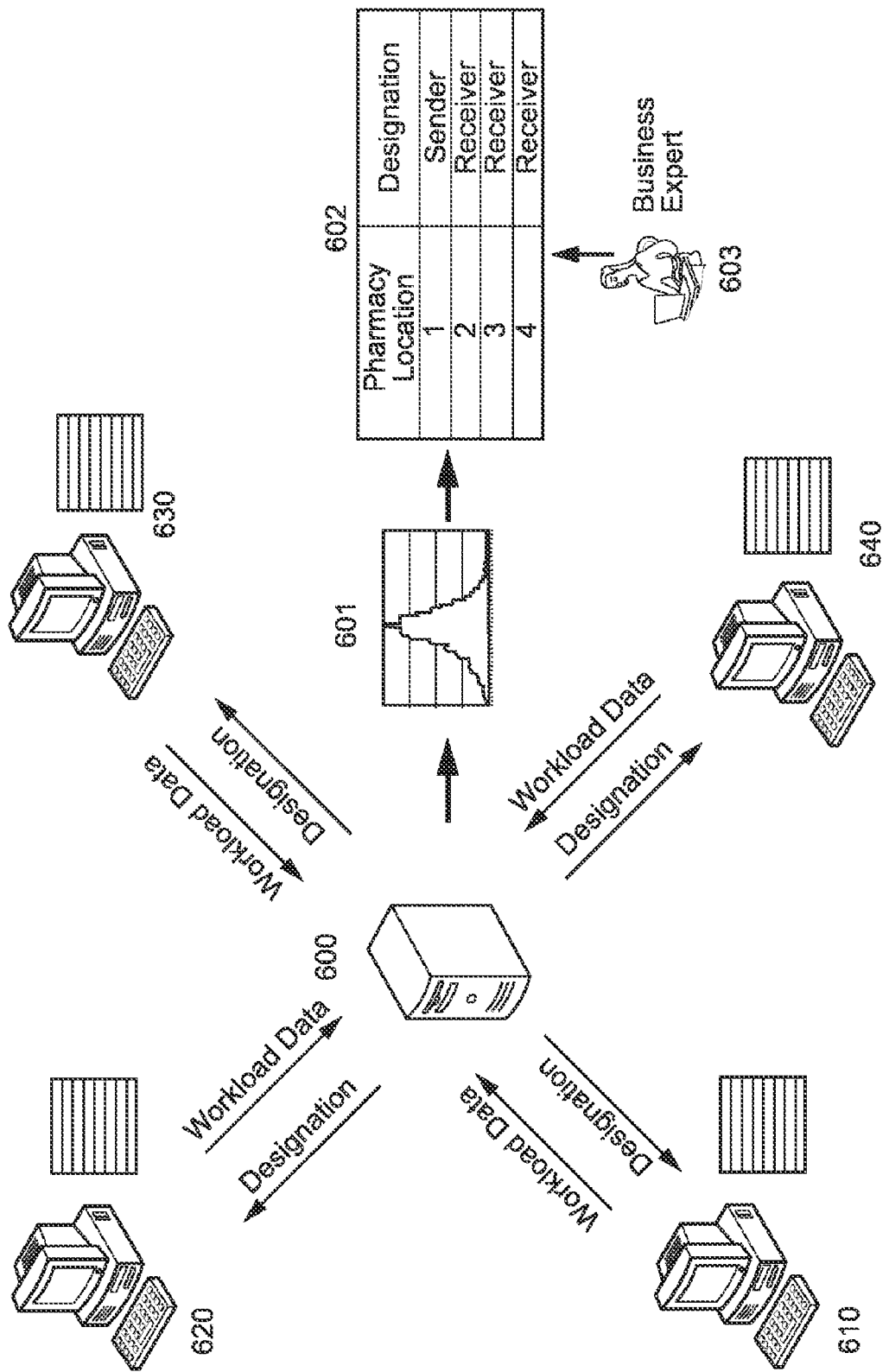
FIG. 6 illustrates an embodiment of a pharmacy network designation system.

As illustrated in FIG. 6, the workload for each pharmacy may be calculated and collected by at least one network computer, e.g., 600, 610, 620, 630, 640. The network computer that collects the workload data may be a network computer at a particular retail store (e.g., 610, 620, 630, 640) and/or a network computer, e.g., 600, at an analysis center that does not perform prescription processing. Among other factors, the prescription count used in the workload calculation may consist of a total number of filled prescriptions in a given amount of time, an average number of prescriptions being processed at a given time, or an average number of prescriptions waiting in a queue for a given amount of time.

Figure 7:
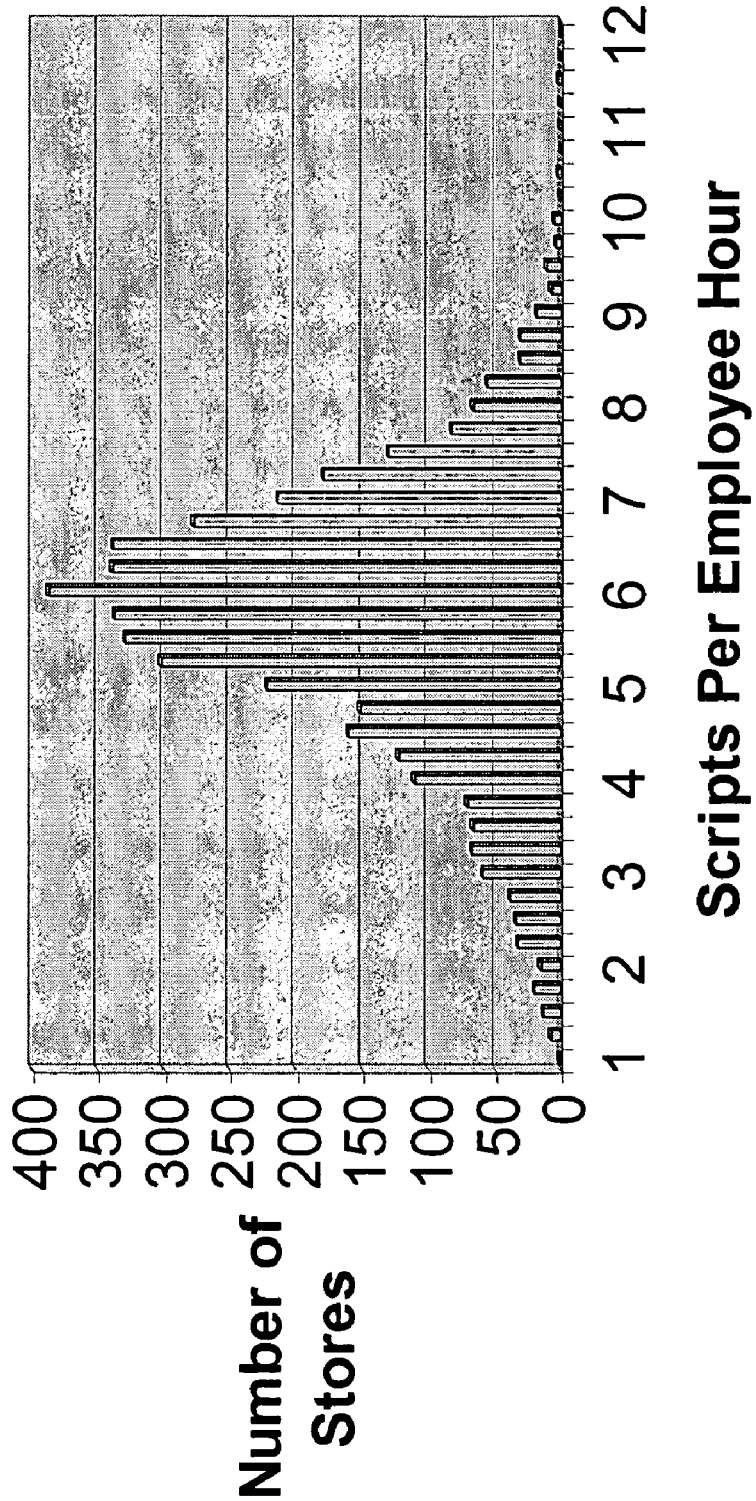
FIG. 7 illustrates a workload distribution graph that may be used to analyze an existing workload distribution.

Once the workload information from the pharmacies is collected, a current workload distribution 601 of a network of pharmacies may then be determined and a redistribution strategy may be analyzed. The analysis may be facilitated by using a distribution graph as illustrated in FIG. 7. Based on the distribution, workload may be redistributed from high workload stores to low workload stores. This may be done to achieve a target workload distribution. For example, in situations where the median distribution is below a certain prescription/man-hour rate, work may be redistributed in order to move the median higher in order to achieve a target average workload. In order to accomplish this, certain pharmacy resources may be identified and designated as receivers or senders. A pharmacy resource may include, for example, employees, equipment, technology, etc. While one embodiment may consider a single store location as a pharmacy resource, in which case the set of resources associated with the store may be considered the pharmacy resource, a pharmacy resource may include pharmacists not necessarily associated with a particular store location, for example, remote pharmacists that work from home. Factors that may be considered in determining a target workload distribution include overhead costs of a pharmacy location, labor costs, taxes, and efficiency factors.

In one embodiment, stores in which workload needs to be redistributed from may be designated as sender stores/resources, while stores in which workload needs to be redistributed to may be designated as receiver stores/resources. Sender stores may be stores in which the workload is higher than a given threshold or average, while receiver stores may be stores in which the workload is lower than a given threshold or average. Thresholds may be determined based on the current workload distribution and target workload distribution. As illustrated in FIG. 6, the designation of a store may be a parameter stored in a central location, such as a table 602 in a server machine 600, and/or a parameter set in a network computer such as 610, 620, 630, or 640. The designations may be manually set or overridden based on an administrator input 603.

Once the stores/resources are designated as senders or receivers, a sender network computer may begin taking unprocessed prescription orders from its queue and sending them to a receiver store/resource queue. The number of prescriptions sent or accepted may be based on a workload level and routing rate that is adjusted in order to meet a target distribution for a particular period of time. For example, a first store may have a workload of 8 prescriptions/man-hour, while the target workload is set at 6 prescriptions/man-hour. The system may set a routing rate such that the first store sends prescriptions to a set of receivers until its workload stabilizes at 6 over a period of time.

Metrics may be taken on a periodic basis such that when a threshold is met, the designation of a store automatically changes. The shorter the period for recalculating workload distribution, the quicker the response for a change in store volume or manpower. For example, should the above mentioned store begin to average only 5 prescriptions/man-hour, the store may be changed from a sender to a receiver. An alternate designation may be non-participating, or neutral. This designation may be placed when the store is performing within a target range at a particular efficiency or when the store is performing within a target workload range. In the above example, if the store is operating at 6 prescriptions/man-hour without intervention (or within a lower and upper threshold around 6 prescriptions/man-hour), it may be designated as non-participating or neutral. It should be noted that the neutral designation may be placed on a store for other reasons, e.g., neutral may be placed on stores that are non-functioning, or non-participating.

Figure 8:
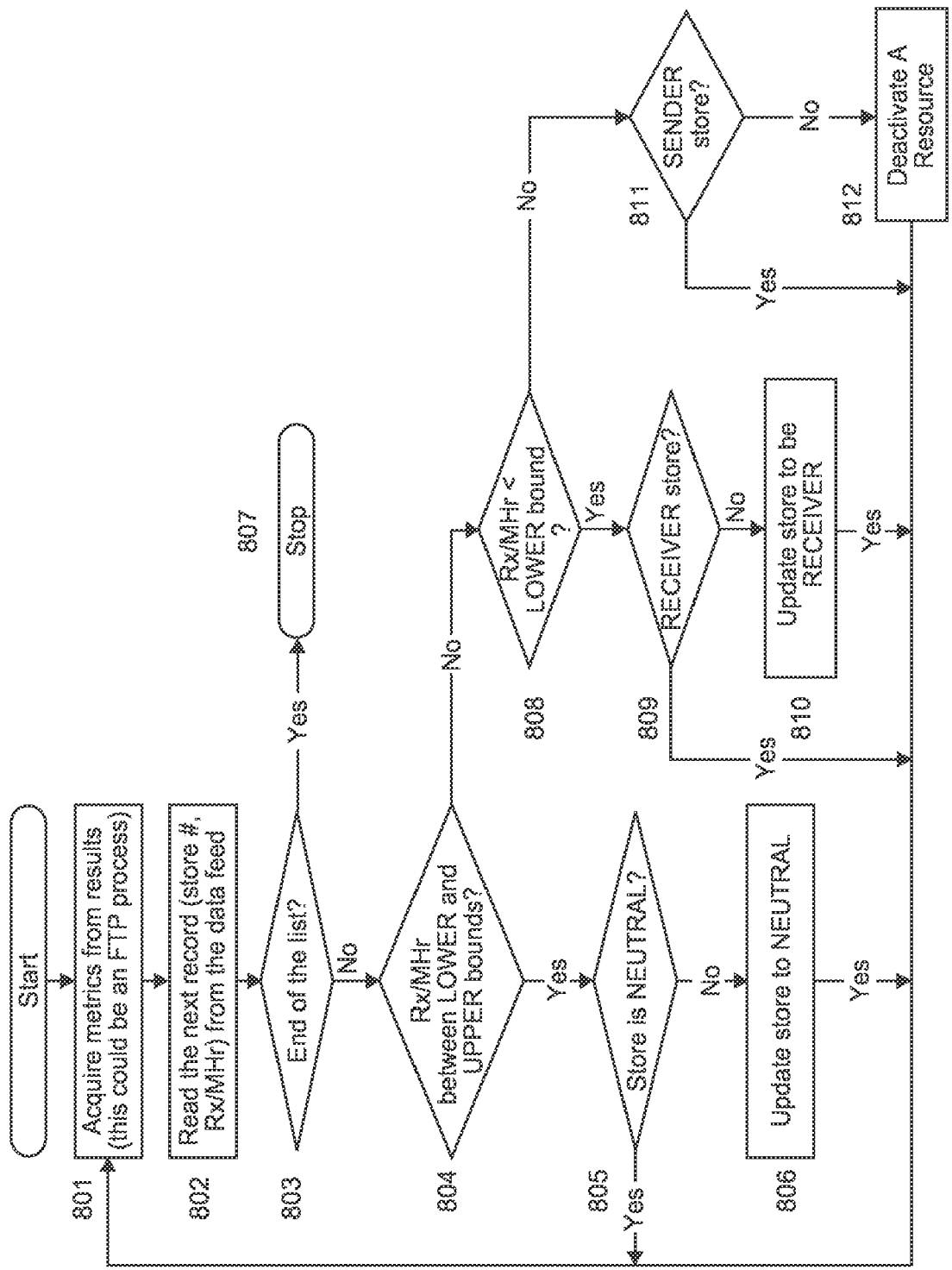
FIG. 8 illustrates a flow chart of the workload distribution process.

The flowchart of FIG. 8 illustrates a designation process. The process starts at block 801, where pharmacy workload metrics are acquired. As mentioned above, this acquisition of metrics may consist of generating a workload distribution. From these metrics, a target workload distribution may be determined. In the embodiment illustrated in FIG. 8, a target workload distribution may result in the determination of a set of threshold values (e.g., maximum and minimum workload values for each store). In blocks 802, 803, and 807, the workload from each store is read. If the end of the list 803 is reached, the process ends 807. Block 804 checks to see if the current store has a workload between a set upper and lower threshold bound. If the workload is within bounds, block 806 designates a store as neutral if it is not already designated neutral in block 805. Block 808 determines if the store workload is below a lower threshold. If so, block 810 designates the store as a receiver, if it is not already designated as a receiver in block 809. If the store workload is greater than an upper threshold, block 812 designates the store as receiver, if it is not already designated a receiver in block 811.

When a store switches designations, it may continue processing the work placed in its queue even if the work is from another pharmacy. However, if the store has been switched from a sender to a receiver or from a receiver to a sender, priority routing may be performed based on ownership of the order. For example, in a store that has switched from a receiver to a sender, the store may first send off work that was not originated from its store. Also, if a prior sender has become a receiver and a prior receiver has become a sender the current sender may direct work back to the receiver that sent it.

Figure 9:
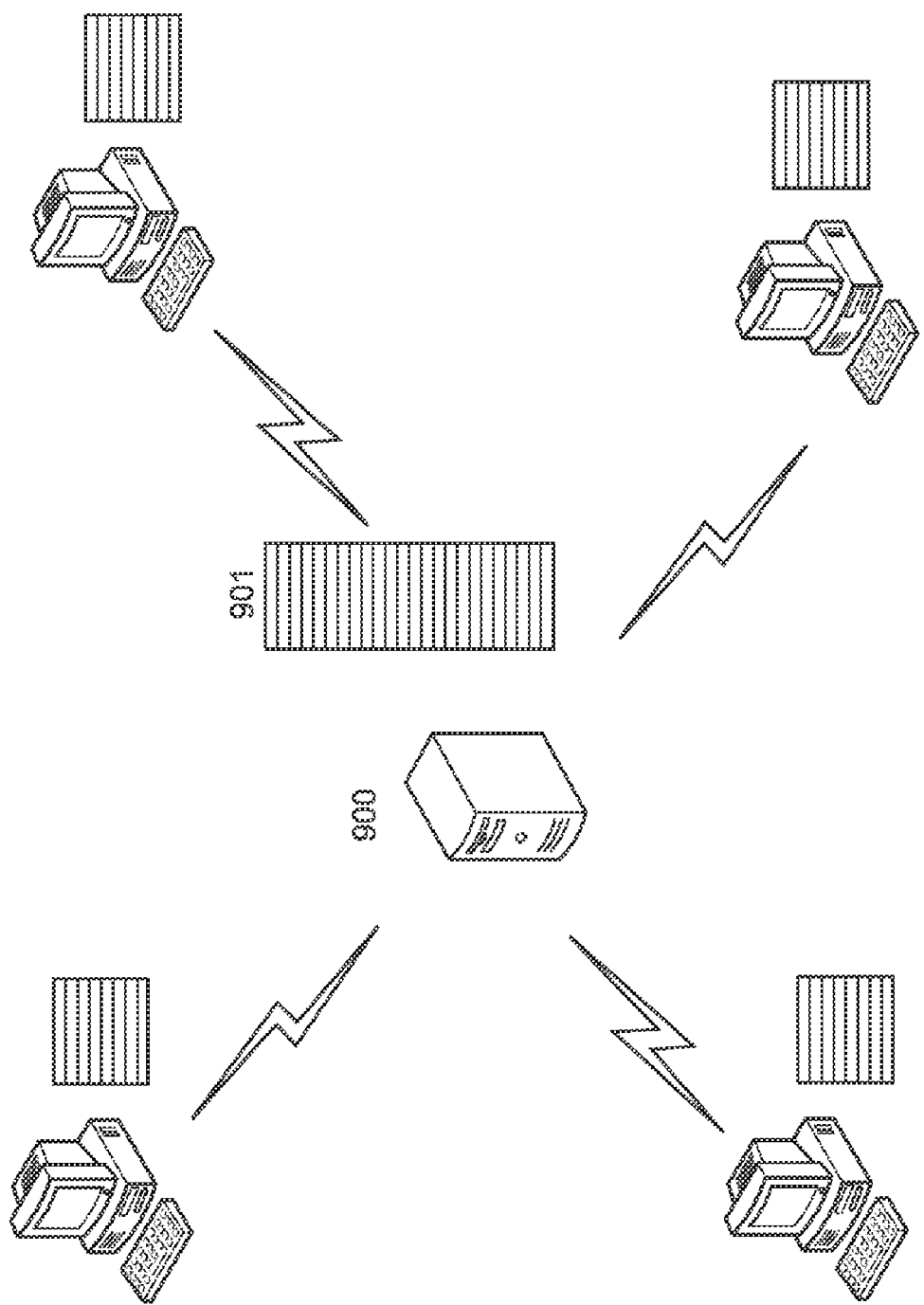
FIG. 9 illustrates an embodiment that uses a central repository queue.

FIG. 9 illustrates an embodiment in which a central server 900 may implement a queue 901 that accepts routed work orders from sender queues. The server acts as a central redistribution repository that will accept work requests from each receiver. In this way, when workload changes induce store designation changes, redistribution is just a matter of changing between work requests from a central location and transmitting work orders to the central location. In this embodiment, completion of information processing for a particular order may trigger printing of a label or instruction set at the printer queue of a distribution resource, e.g., a pharmacy location, a mail order facility, etc., for filling and dispensing.

Additional metrics may be used to determine the efficacy of a workload distribution. For example, a cost metric may be used to determine if the increase in the average prescriptions/man-hour rate for the network translates into a cost savings. This may be done by factoring in the number of prescriptions sent to the receiving stores, the number of prescriptions completed by the receiving stores, and then calculating the financial benefit to a store based on possible missed prescriptions. This report may be called a missed opportunity report.

Workload distribution may be based on a capacity of a network resource to process product demand. In the case of a pharmacy network system, demand may be based on the number of prescriptions that need to be processed in a given amount of time, e.g., a promised delivery time. (Queued prescriptions may be arranged by promised time, and consequently, demand may be based on the promised times of prescription orders in a queue.) Pharmacy resource capacity may be based on the rate at which the resource can process a number of prescriptions. This rate may be estimated based on historic data for the resource. For example, metrics may be taken to determine the average time necessary for a pharmacy resource to process a number of prescription orders. The capacity of the resource can then be estimated by calculating the amount of time necessary to process the prescription orders in its queue and comparing this to a desired time, such as a promised delivery time, for the prescription orders. If the estimated finish time approaches or exceeds the desired time, then the pharmacy resource may have insufficient capacity and be designated as a sender. If the estimated finish time is less than the desired time by a threshold, then the pharmacy resource may have excess capacity and may be designated as a receiver. The threshold may be based, for example, on the amount of time needed for a resource to process an additional order within the desired time for that order. In one embodiment, the promised time of queued work orders for a pharmacy resource may be averaged and the pharmacy resource may be designated a receiver or sender based on whether the averaged promised time is above or below a threshold.

Workload distribution may be further based on product type and resource type. In a pharmacy system comprising a network of pharmacy resources, each pharmacy may be outfitted with identical equipment, inventory, and personnel for processing standard drug prescription orders. However, there are non-standard or non-traditional drugs that may require different equipment, special materials, and/or different technical expertise to process. Outfitting every facility with similar equipment and inventory to account for non-traditional drugs could be prohibitively expensive. Providing expert personnel at each store location in a network may also be difficult, if not impossible. Also, more often than not, the demand for non-traditional drugs and even a portion of traditional drugs, is not substantial enough to justify an additional expenditure in equipment, inventory, and human resources for each store.

A pharmacy system may thus assign or designate certain resources, e.g., facilities or personnel, to process a portion of a prescription order based on drug type. The assignment may be based on a demand for the drug type and/or a capacity of a resource to process the drug type. In this case, the capacity of the resource may be based on the efficiency and cost of using the pharmacy resource, not just its capacity to fill a demand in a given time. A workload distribution system may accordingly route prescription orders for specific drug types primarily to the designated pharmacy resources having the capacity to process the drug types, thereby leveraging pharmacy resource expertise and/or economies of scale. The designated pharmacy resource may be called a process center for the specific drug type.

Figure 10:
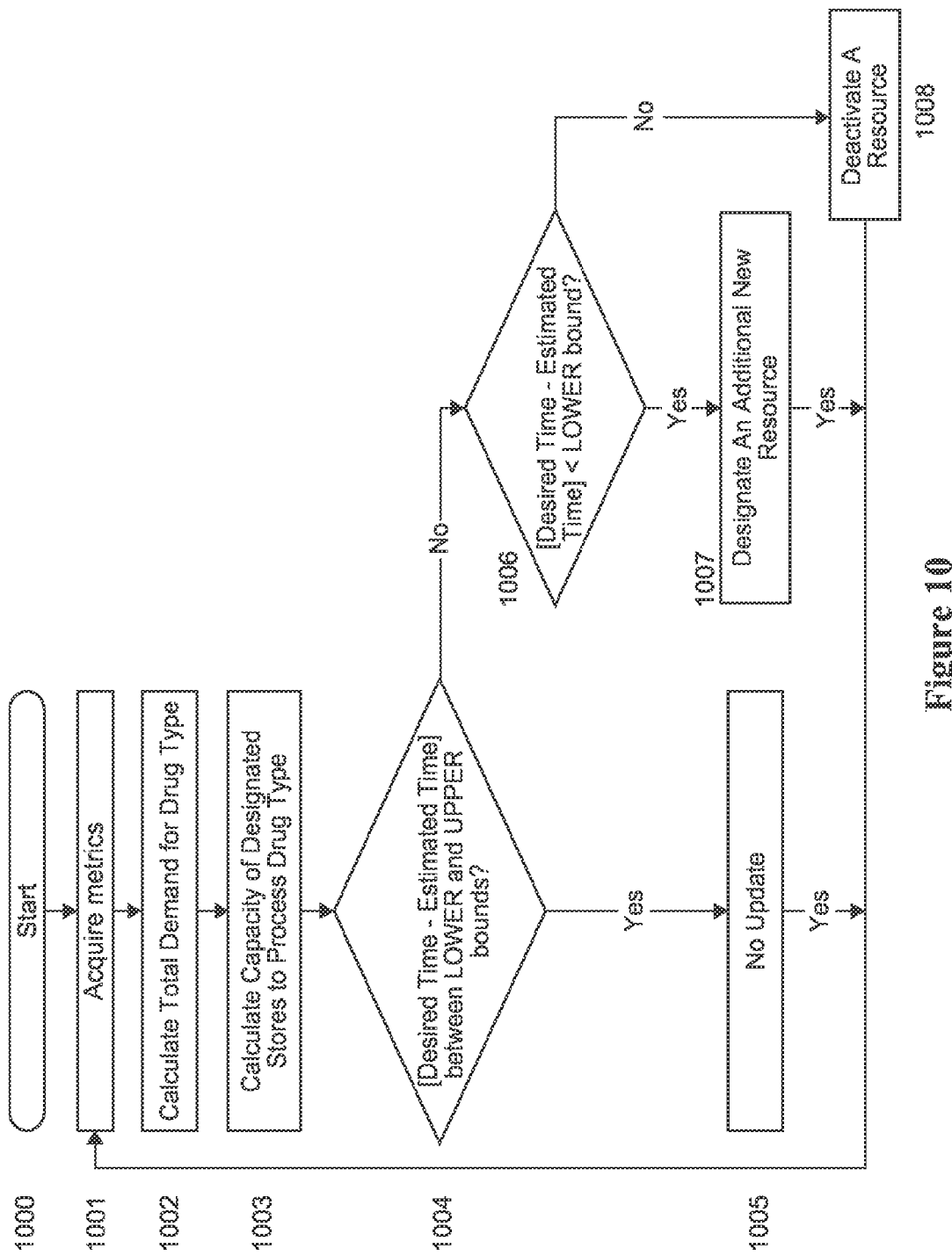
FIG. 10 illustrates a resource assignment process.

In one embodiment, assigning a pharmacy resource to process the prescription order may be based on minimizing a difference between the system demand for the drug type and the capacity of a set of pharmacy resources. FIG. 10 illustrates this embodiment. Metrics are acquired in a first block 1001. The demand for a drug type is determined 1002 by taking the total number of prescription orders in the network associated with a drug type. The capacity of pharmacy resources assigned to process the drug type may be considered by first calculating an estimated time for processing the prescription orders for the drug type 1003. When the estimated time of processing by the assigned resources is less than a desired time by a threshold amount (e.g., a safety margin) no further assignments are necessary 1005. When a single pharmacy resource is insufficient to process the demand in a desired time 1006, more pharmacy resources may be assigned to process the drug type 1007. When demand for a drug type falls, the system may determine that less pharmacy resources need to be allocated to process a drug type and may reduce the number of designated stores 1008 processing that drug type. This may be done incrementally and may be based on a set of thresholds that are determined based on safety margins. Alternatively, in addition to calculating the estimated time for processing the demand, a capacity measure may include calculating a cost efficiency. For example, given that a first pharmacy resource and a second pharmacy resource may process the demand in the desired time, the system may determine that the first pharmacy resource is cheaper to use than the second resource and assign the first resource as a process center. The system may then route prescriptions primarily to the first resource.

Figure 11:
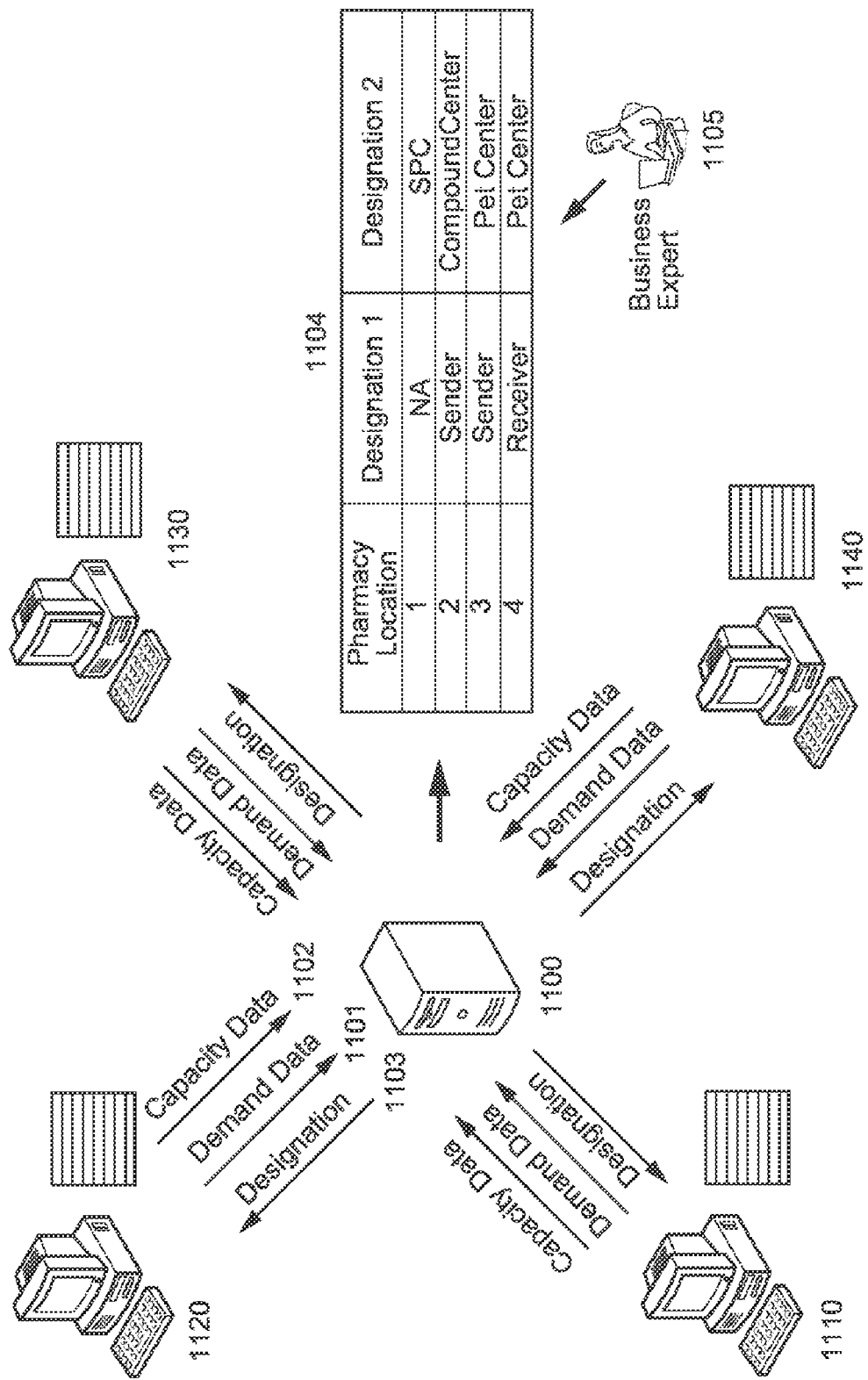
FIG. 11 illustrates a resource assignment system.

FIG. 11 illustrates a computer system for assigning functions to a network of pharmacy resources. A server 1100 may receive demand data 1101 and capacity data 1102 from a set of pharmacy client computers 1110-1140 associated with pharmacy resources. The demand data and capacity data may be used to determine assignments/designations 1103 for pharmacy resources. These assignments may be stored in a table 1104 or other data object. A business expert 1105 may provide parameters used to help determine the assignments.

Table 1104 illustrates that each pharmacy resource may function in more than one capacity and may have multiple designations. For example, pharmacy location 2, 3, and 4, as illustrated in table 1104, may function both as retail stores receiving or sending traditional prescription orders as well as a processing center for a particular function. (It should be noted that a pharmacy resource may have more than two designations.)

When a pharmacy resource is designated as a process center, that pharmacy resource may be a primary receiver for prescription orders associated with a drug type that the pharmacy resource is assigned to process. If there is only one pharmacy resource assigned to process a drug type, for example compound drugs, then all compound drug prescriptions in the network may be routed to that pharmacy resource. However, if demand exceeds the capacity of the single resource, more pharmacy resources may be assigned to handle the workload. This is the case illustrated in 1104, where two pharmacy resources (locations 3 and 4) are designated pet centers.

Determining capacity of the resource may involve determining the existence of equipment, availability of materials at the facility to process the drug type, and availability of the equipment. Availability of the equipment may be based on the existing workload of the equipment. Availability of equipment may also be based on a configuration of the equipment. For example, identical equipment may be used to process two different drug types, but a different equipment setup may be required to produce each drug type. In this case, equipment capacity may take into account a transition time required to configure the equipment to process a prescription order associated with a different drug type. Efficiency of the pharmacy resource or equipment may also be based on the transition time.

A pharmacy resource may be an individual pharmacist. Pharmacists for performing specialty drug processing may be located in a number of different locations, including retail stores, other specialty stores, or home locations. A distribution table such as 1200 in FIG. 12, may be accessed to determine pharmacist assignments 1250, availability information 1230, and location 1220. Whenever additional pharmacists are needed to handle increased demand or other workload events, the distribution table may be accessed to determine which additional resources may be activated/assigned. The table may be stored on a server and updated accordingly.

In one embodiment, determining the capacity of a pharmacist may include determining the availability of the pharmacist to process a drug type. This may be based on a pharmacist work schedule 1230. Determining the capacity of the pharmacist may also be based on an expertise level 1240 of the pharmacist and a labor cost of the pharmacist. The expertise level may be based on a certification of a pharmacist to perform processing for specialized drugs. This certification may be based on legal standards. The expertise level may also be determined by a pharmacy company. For example, the expertise level may be based on an accuracy rating of the pharmacist and/or efficiency of the pharmacist, where efficiency may be based on the pharmacist's rate of processing a specific drug type.

Figure 13:
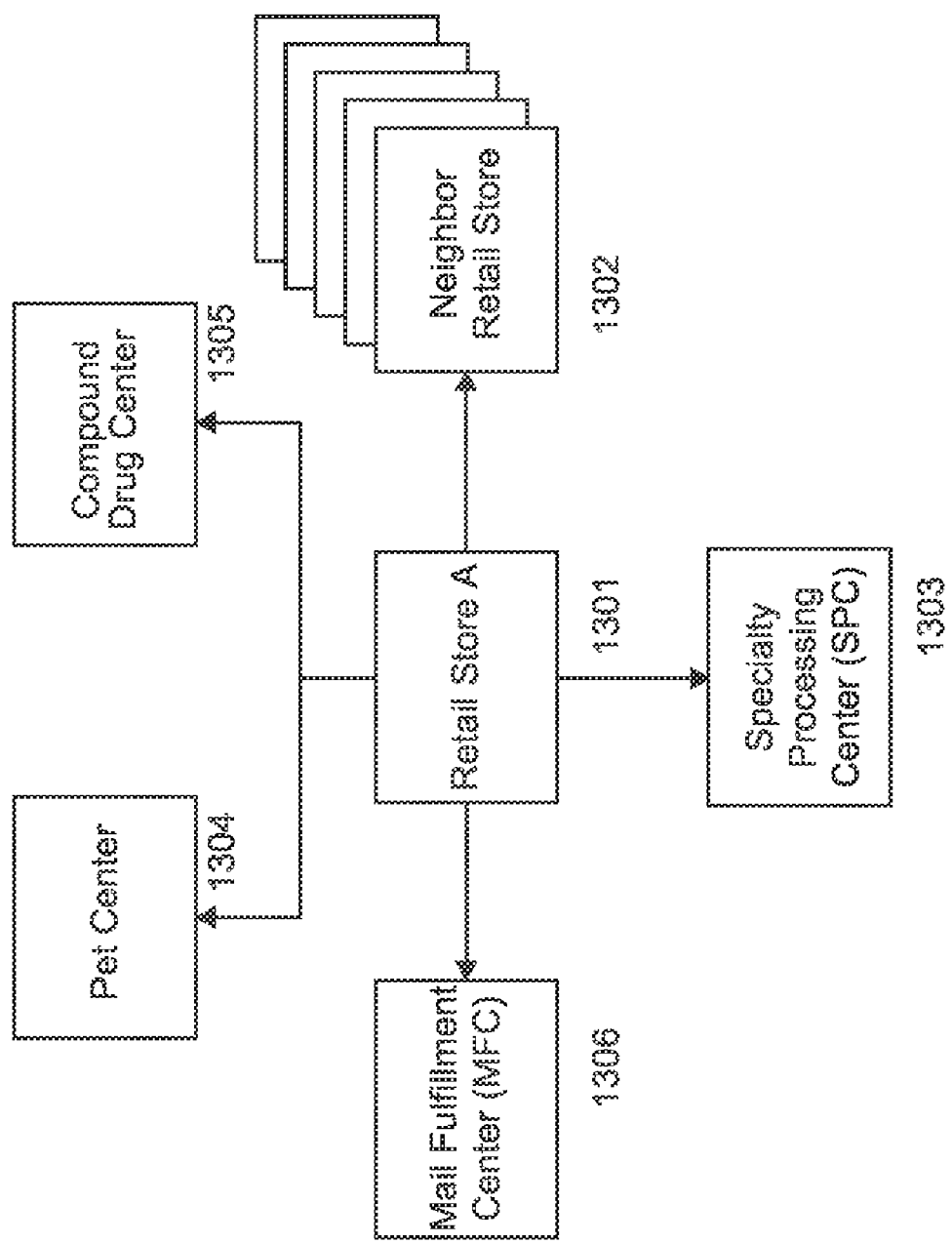
FIG. 13 illustrates a distributed processing environment for a pharmacy network.

FIG. 13 illustrates a pharmacy network where process functions are assigned to specialized pharmacy resource units. In this network, a retail store A 1301 may be connected to a set of neighbor retail stores 1302. The network may also have specialized facilities such as a special processing center ("SPC") 1303 which may be a separate facility that houses a set of experts. This set of experts may be more efficient at processing specialty drugs. The work orders for specialty drugs may be routed primarily to the SPC, thereby aggregating specialty drug processing at a cost efficient resource. Additionally, there may be facilities that contain specialized equipment for less common medications such as pet medicine or compound drugs. These resources may also be housed in separate facilities, e.g., a pet center 1304 or a compound drug center 1305 and prescriptions orders for pet medication and compound drugs may be routed to their respective processing centers for faster processing. Also, consolidation of certain common process functions, such as fulfillment and mailing, may also increase the speed at which general prescriptions are processed. Thus, a mail fulfillment facility ("MFC") 1306 having both equipment and personnel focused solely on fulfillment and mailing may also increase network efficiency.

While FIG. 13 illustrates a single function assignment to a pharmacy resource, e.g., pet, specialty, and compound centers, these facilities are not necessarily limited to only one function. For example, an SPC facility may have the capability to also serve as a retail store. This cross-functional capacity allows for assignment of functionality based on network demand and efficiency. For example, while the equipment to process compound drugs may not be provided at each facility, a subset of retail facilities may hold equipment capable of processing compound drugs. Because the demand for compound drugs may not justify the cost of operating all the equipment at one time, only a subset of stores may be assigned to process compound drugs. Thus, in one embodiment, when demand for compound drugs is not high, only a few of the resources having compound making capabilities may be designated as compound centers and process compound prescription orders Meanwhile, the non-assigned facilities may operate in another capacity. When demand increases, more stores/facilities having compound equipment may be made available and designated as compound facilities to process the extra demand, even while the same facility continues to function in other roles.

Workload distribution may also be based on anticipated capacity changes of a pharmacy resource. For example, in emergency situations, (e.g., a natural disaster causing evacuation of pharmacists) work may be manually redirected to non-affected locations and stores. In another example, there may be anticipated intermittent staffing and/or availability changes (e.g., equipment maintenance periods, staff vacations, etc.) which may cause the efficiency of a resource to decrease. In this situation, a target workload distribution may involve placing a smaller workload on pharmacy resources in which there is an anticipated shortage in capacity. The determination of the target workload distribution may also consider the workload backlog at a particular location and adjust that location up or down accordingly. It should be noted that an anticipated staffing shortage may be accounted for when calculating the workload for the store and/or when determining an appropriate target workload distribution. Furthermore, in addition to anticipating staffing changes, an embodiment of the claims may proactively adjust staffing in order to effect workload of a pharmacy to achieve a target workload distribution of the network.

What is claimed:

1. A method of managing drug prescription orders within a network of pharmacy resources, comprising:
    identifying a drug type corresponding to an incoming prescription order at a first computing device of an information processing system connecting the network of pharmacy resources, the first computing device being associated with a first pharmacy resource;
    determining that a second pharmacy resource in the network of pharmacy resources is assigned as a designated processing center for at least a portion of prescription orders for the drug type, wherein determining that the second pharmacy resource is assigned as the designated processing center comprises determining that the second pharmacy resource is assigned as the designated processing center based on a network demand for the drug type and a local capacity of the second pharmacy resource to process the at least a portion of prescription orders for the drug type; and
    sending, by the first computing device via the information processing system to a second computing device associated with the second pharmacy resource, at least a portion of the incoming prescription order to the second pharmacy resource for processing, wherein processing each prescription order includes performing physical preparation of each prescription order and performing information processing of each prescription order, and wherein performing information processing of each prescription order includes authenticating each prescription order, validating any third party provider information, collecting payment information, and referencing drug information associated with the drug type.

2. The method of claim 1, wherein determining that the second pharmacy resource is assigned as the designated processing center comprises obtaining an indication from a third computing device via the information processing system.

3. The method of claim 2, wherein the indication obtained from the third computing device is based on a local capacity of one or more particular pharmacy resources in the network of pharmacy resources to process the at least a portion of prescription orders for the drug type.

4. The method of claim 1, further comprising indicating, by the first computing device to another computing device via the information processing system, at least one of: a local capacity of the first pharmacy resource to process the at least a portion or another portion of prescription orders for the drug type, or a tally of prescription orders associated with the drug type at the first pharmacy resource.

5. The method of claim 1, further comprising:
    determining a delivery pharmacy resource in the network of pharmacy resources corresponding to a desired delivery location of the incoming prescription order, and
    indicating the delivery pharmacy resource to the second computing device.

6. The method of claim 1, further comprising processing at least a part of any remaining portion of the incoming prescription order at the first computing device associated with the first pharmacy resource.

7. The method of claim 1, further comprising:
    determining that a third pharmacy resource in the network of pharmacy resources is a different designated processing center for at least a different portion of prescription orders for the drug type; and
    sending, by the first computing device via the information processing system to a third computing device associated with the third pharmacy resource, at least a different portion of the incoming prescription order to the third pharmacy resource for processing.

8. The method of claim 1, wherein:
    the second pharmacy resource in the network of pharmacy resources includes a facility, and
    determining that the second pharmacy resource is assigned as the designated processing center for the at least a portion of prescription orders for the drug type is based on at least one of: an existence of equipment at the facility to process the drug type, an availability of the equipment at the facility to process the drug type, or an availability of materials at the facility to process the drug type.

9. The method of claim 1, wherein:
the second pharmacy resource in the network of pharmacy resources is associated with a pharmacy employee capable of processing the at least a portion of prescription orders for the drug type, and
determining that the second pharmacy resource is assigned as the designated processing center for the at least a portion of prescription orders for the drug type is based on at least one of: an availability of the pharmacy employee, an efficiency of the pharmacy employee, or a labor cost associated with the pharmacy employee.

10. The method of claim 1, wherein determining that the second pharmacy resource is assigned as the designated processing center is based on an availability of the drug type at the second pharmacy resource.

11. A system for managing drug prescription orders within a network of a plurality of pharmacy resources, the system comprising:
a set of computers coupled to an information processing system connecting the network of the plurality of pharmacy resources, wherein each of at least a subset of the set of computers is associated with at least one of the plurality of pharmacy resources and is programmed with instructions for:
identifying a drug type corresponding to an incoming prescription order;
determining that a first pharmacy resource of the plurality of pharmacy resources is assigned as a designated processing center for at least a portion of prescription orders for the drug type, wherein the first pharmacy resource of the plurality of pharmacy resources is assigned as the designated processing center for the at least a portion of prescription orders for the drug type based on at least one of: an availability of the drug type of the first pharmacy resource, or a local capacity of the first pharmacy resource for processing the at least a portion of prescription orders for the drug type; and
sending, via the information processing system to a first computer associated with the first pharmacy resource, at least a portion of the incoming prescription order to the first pharmacy resource for processing, wherein processing each prescription order includes performing physical preparation of each prescription order and performing information processing of each prescription order, and wherein performing information processing of each prescription order includes authenticating each prescription order, validating any third party provider information, collecting payment information, and referencing drug information associated with the drug type.

12. The system of claim 11, wherein each of the at least the subset of the set of computers is programmed with further instructions for:
obtaining an indication, from a second computer via the information processing system, that the first pharmacy resource in the network of the plurality of pharmacy resources is assigned as the designated processing center for the at least a portion of prescription orders for the drug type; and
indicating, to the second computer, at least one of: a local capacity of a pharmacy resource corresponding to each of the at least the subset of the set of computers for processing the at least a portion or another portion of prescription orders for the drug type, or a tally of prescription orders associated with the drug type at the pharmacy resource corresponding to each of the at least the subset of the set of computers.

13. The system of claim 11, wherein each of the at least the subset of the set of computers is programmed with further instructions for:
determining a delivery pharmacy resource in the network corresponding to a desired delivery location of the incoming prescription order, and
indicating the delivery pharmacy resource to the first computer.

14. The system of claim 11, wherein each of the at least the subset of the set of computers is programmed with further instructions for at least one of:
processing at least a first part of any remaining portion of the incoming prescription order, or
determining that a second pharmacy resource in the network of the plurality of pharmacy resources is a designated processing center for at least a second portion of prescription orders, and sending, via the information processing system to a third computer associated with the second pharmacy resource, at least a second portion of the incoming prescription order to the second pharmacy resource for processing.

15. A method of distributing pharmacy prescription processing workload in a network of a plurality of pharmacy resources, comprising:
associating each of the plurality of pharmacy resources with a different computer of a plurality of computers;
communicatively coupling the plurality of computers via an information processing system;
determining a network capacity of the plurality of pharmacy resources for a drug type based on at least one of: a local capacity of each of the plurality of pharmacy resources for processing prescription orders for the drug type, or a local tally of prescription orders for the drug type at each of the plurality of pharmacy resources;
determining a network demand for the drug type, wherein the network demand for the drug type is based on a total number of prescription orders for the drug type to be filled in the network of the plurality of pharmacy resources;
assigning each of a subset of the plurality of pharmacy resources as a designated processing center for processing at least a portion of prescription orders for the drug type, the assigning based on the network demand and a part of the local capacities of the plurality of pharmacy resources for processing prescription orders for the drug type, wherein the part of the local capacities corresponds to processing the at least a portion of prescription orders for the drug type; and
indicating, to at least one of the plurality of computers associated with a particular pharmacy resource, at least one of the subset of the plurality of pharmacy resources that are assigned as designated processing centers,
wherein:
each of the designated processing centers is enabled to process the at least a portion of prescription orders for the drug type,
processing entire prescription orders for the drug type includes performing physical preparation and performing information processing, and
at least one of the plurality of pharmacy resources is enabled to independently process a particular entire prescription order, and performing information processing for the particular prescription order for the drug type includes authenticating the particular prescription order, validating third party provider information, collecting payment information, and referencing drug information corresponding to the drug type.

16. The method of claim 15, further comprising:
receiving incoming prescription orders at a first computer associated with a first pharmacy resource in the network,
identifying, at the first computer, a particular incoming prescription order associated with the drug type, and
routing, by the first computer via the information processing system, at least a portion of the particular incoming prescription order to a first designated processing center corresponding to the drug type.

17. The method of claim 16, further comprising indicating, by the first computer to another computer via the information processing system, at least one of the local capacity of the first pharmacy resource for processing prescription orders for the drug type or a tally of prescription orders associated with the drug type at the first pharmacy resource.

18. The method of claim 15, further comprising at least one of:
designating a larger subset of the plurality of pharmacy resources if a current network demand for the drug type exceeds a current capacity of a current subset of the plurality of pharmacy resources for processing prescription orders for the drug type, or
designating a smaller subset of the plurality of pharmacy resources if the current capacity of the current subset of the plurality of pharmacy resources for processing prescription orders for the drug type exceeds the current network demand for the drug type by a threshold.

19. The method of claim 15, wherein at least one of:
each of the plurality of pharmacy resources includes a pharmacy employee, and wherein determining the local capacity of each of the plurality of pharmacy resources for processing prescription orders for the drug type comprises estimating a rate of processing the drug type by the pharmacy employee; or
each of the plurality of pharmacy resources includes a facility, and wherein determining the local capacity of each of the plurality of pharmacy resources for processing prescription orders for the drug type is based on at least one of an availability of equipment corresponding to processing the drug type at the facility or an availability of materials corresponding to the drug type at the facility.

* * * * *